United States Patent [19]

Albrecht et al.

[11] 3,932,424

[45] Jan. 13, 1976

[54] BIS-BASIC ETHERS OF CARBAZOLE

[75] Inventors: William L. Albrecht; Robert W. Fleming, both of Cincinnati, Ohio

[73] Assignee: Richardson-Merrell Inc., Wilton, Conn.

[22] Filed: July 31, 1974

[21] Appl. No.: 493,271

Related U.S. Application Data

[63] Continuation of Ser. No. 46,462, June 15, 1970, abandoned.

[52] U.S. Cl. .......... 260/293.61; 260/315; 424/267; 424/274
[51] Int. Cl.² ................................. C07D 209/88
[58] Field of Search .................... 260/315, 293.61

[56] References Cited
UNITED STATES PATENTS

3,673,191  6/1972  Albrecht et al. ............... 260/293.57

OTHER PUBLICATIONS

Medicinal Chemistry, Burger, Vol. I, (1951), pp. 43-45 & 48.

*Primary Examiner*—Sherman D. Winters
*Attorney, Agent, or Firm*—George W. Rauchfuss, Jr.; Eugene O. Retter

[57] ABSTRACT

The novel bis-basic ethers of carbazole of the present invention have useful antiviral properties. These new compounds are represented by the formula

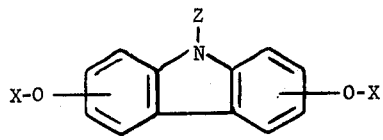

wherein Z is hydrogen or lower alkyl having from 1 to 4 carbon atoms; and each X is

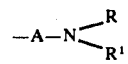

A. the group -A-N wherein each A is a straight or branched alkylene chain having from 2 to 6 carbon atoms; R and $R^1$ are individually hydrogen or lower alkyl having from 1 to 6 carbon atoms; or each set of R and $R^1$ taken together with the nitrogen atom to which they are attached is a saturated monocyclic heterocyclic group such as pyrrolidino or piperidino; or B. the group

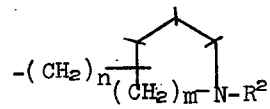

wherein $n$ is a whole integer from 0 to 2, $m$ is 1 or 2, and $R^2$ is hydrogen or lower alkyl having from 1 to 4 carbon atoms.

This invention also includes pharmaceutically acceptable acid addition salts of the bases represented by Formula I. These new compounds may be prepared by several different methods which are described.

7 Claims, No Drawings

BIS-BASIC ETHERS OF CARBAZOLE

This is a continuation of application Ser. No. 46,462, filed June 15, 1970, now abandoned.

This invention relates to new bis-basic ethers of carbazole which have useful antiviral properties and to processes for preparing the same.

The new compounds of this invention are represented by the general formula

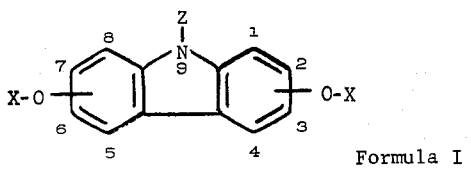

Formula I wherein Z is hydrogen or lower alkyl having from 1 to 4 carbon atoms; and each X is A. the group

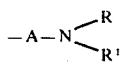

wherein each A is a straight or branched alkylene chain having from 2 to 6 carbon atoms and which separates the amino nitrogen and oxygen by at least 2 carbon atoms; R and $R^1$ are individually hydrogen or lower alkyl having from 1 to 6 carbon atoms; or each set of R and $R^1$ taken together with the nitrogen atom to which they are attached is a saturated monocyclic heterocyclic group such as pyrrolidino or piperidino; or B. the group

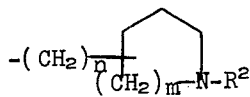

wherein $n$ is a whole integer of from 0 to 2, $m$ is 1 or 2, and $R^2$ is hydrogen or lower alkyl having from 1 to 4 carbon atoms.

The compounds of this invention include both the base form represented by Formula I and pharmaceutically acceptable acid addition salt of the base form.

As can be seen from the above general Formula I, one basic ether group, that is, —O—X, is attached to each of the two benzenoid rings of the carbazole ring system. Thus one of these groups can be linked to the carbazole ring system by replacement of any one of the hydrogen atoms in positions 1 through 4, while the second of these groups can replace any one of the hydrogen atoms in positions 5 through 8. Preferably, the basic ether groups are in either the 1,7- or the 3,6-position of the carbazole ring system.

Although one of the two X groups in a compound of the above general Formula I can be

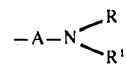

and the other can be the group

it is preferred that both X groups are the same as more fully shown by the following general Formula II and III:

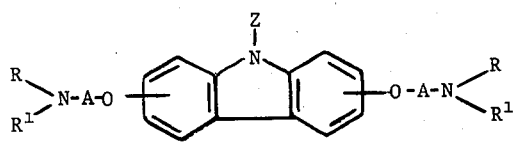

Formula II

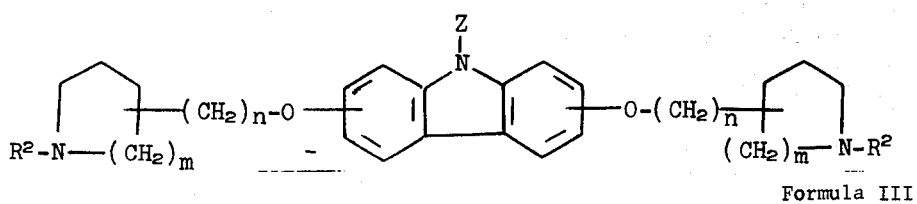

Formula III

In the above general Formulas II and III, the various groups Z, A, R, $R^1$, $R^2$, $n$ and $m$ have the same meanings given hereinbefore.

In the compounds of the above Formulas II and III, Z represents hydrogen or lower alkyl having from 1 to 4 carbon atoms. When Z represents lower alkyl having from 1 to 4 carbon atoms, such group may be attached to the tricyclic heterocyclic nitrogen atom through either the primary or secondary carbon atom of the lower alkyl group. Illustrative of lower alkyl groups as represented by Z there can be mentioned for example: methyl, ethyl, propyl, isopropyl, butyl and the like.

Each of the symbols A in the above Formula II is an alkylene group having from 2 to 6 carbon atoms which can be straight chained, or branched chained, and which separates the ether oxygen from the amino nitrogen by an alkylene chain of at least 2 carbon atoms. Each of the alkylene groups represented by A can be the same or different, although preferably both of these groups are the same. Illustrative of alkylene groups represented by A there can be mentioned for example: 1,2-ethylene, 1,3-propylene, 1,4-bytylene, 1,5-pentylene, 1,6-hexylene, 2-methyl-1,4-butylene, 2-ethyl-1,4-butylene, 3-methyl-1,5-pentylene and the like. Preferably A is an alkylene group having from 2 to 4 carbon atoms.

In the compounds of Formula II each amino group, that is,

can be a primary, secondary or tertiary amino group. Each R and R¹ is individually hydrogen or lower alkyl having from 1 to 6 carbon atoms; or each set of R and R¹ taken together with the nitrogen atom to which they are attached is a saturated monocyclic heterocyclic group. Preferably each of the

groups is a tertiary amino group.

Illustrative of lower alkyls which can be represented by each R or R¹ in the compounds of Formula II there can be mentioned straight or branched chain alkyls, such as, for example, methyl, ethyl, n-propyl, isopropyl, n-butyl, tertiary butyl, n-pentyl, n-hexyl and the like.

Illustrative of monocyclic heterocyclic groups which are represented by each set of R and R¹ taken together with the nitrogen atom to which they are attached in the compounds of Formula II there can be mentioned for example pyrrolidino and piperidino.

Each of the saturated heterocyclic groups of the compounds of Formula III can be attached to the ether oxygen through an alkylene linkage of 1 or 2 carbon atoms, for example, methylene or 1,2-ethylene, or each saturated heterocyclic group can be attached to the ether oxygen through a ring carbon atoms of the heterocyclic group when n is zero. The saturated heterocyclic group is attached to either the alkylene group or oxygen through a carbon atom of the ring by replacement of one of the hydrogen atoms of the ring. The heterocyclic groups in the compounds represented by Formula III can be 5- or 6-membered rings, that is, $m$ is 1 or 2. As examples of various groups represented by

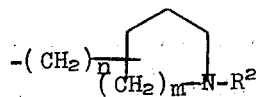

in the compounds of the present invention there can be mentioned for example: N-methyl-4-piperidyl, N-methyl-3-piperidyl, N-ethyl-3-pyrrolidyl, (N-methyl-4-piperidyl)methyl, (N-methyl-3piperidyl)methyl, 2-(2-piperidyl)ethyl and the like.

Each R and R¹ group in the compounds of Formula II and R² group in the compounds of Formula III can be the same or different in each of the basic ether groups attached to the carbazole ring system. Preferably, however, both of the R groups, R¹ groups or R² groups in each compound are the same. Preferred substituents for the R and R¹ groups are alkyl radicals having from 1 to 6 carbon atoms. Preferred substituents for the R² groups are alkyl radicals having from 1 to 4 carbon atoms.

As examples of base compounds of this invention which are represented by the general Formula II there can be mentioned for example: 3,6-bis-(4-aminobutoxy)-N-ethylcarbazole, 3,6-bis[2-(diethylamino)ethoxy]-N-ethyl-carbazole, 3,6-bis[2-(diisopropylamino)ethoxy]carbazole, N-ethyl-3,6-bis-[5-(di-n-propylamino)-pentoxy]carbazole, 1,8-bis[3-(di-n-butylamino)-propoxy]-carbazole, N-ethyl-3,6-bis[3-(dimethylamino)-2-methylpropoxy]carbazole, 1,7-bis[3-(dimethylamino)propoxy]-N-methylcarbazole, N-ethyl-3,6-bis[2-(pyrrolidino)ethoxy]carbazole, N-ethyl-3,6-bis[3-(piperidino)propoxy]carbazole and the like.

As examples of base compounds of this invention which are represented by general Formula III there can be mentioned for example: N-ethyl-3,6-bis[2-(N-methyl-4-piperidyl)ethoxy]carbazole, N-ethyl-3,6-bis(N-methyl-4-piperidyloxy)carbazole, 1,7-bis[2-(N-methyl-4-piperidyl)ethoxy]carbazole, 3,6-bis(N-ethyl-3-pyrrolidyloxy)N-propylcarbazole and the like.

The pharmaceutically acceptable acid addition salts of the base compounds of this invention are those of any suitable inorganic or organic acids. Mono- or bis-acid addition salts can be formed, although in practice, the bis-salts are usually isolated. Also, the salts can be hydrated, for example, monohydrate, or substantially anhydrous. Suitable inorganic acids for preparing the salt form are, for example, mineral acids, such as, hydrochloric, hydrobromic, sulfuric or phosphoric acids and the like. Suitable organic acids are, for example, citric acid, malic acid, glycolic acid, lactic acid, tartaric acid, malonic acid, succinic acid, maleic acid, fumaric acid and the like.

The compounds of the present invention can be administered to prevent or inhibit infections of: picornaviruses, for example, encephalomyocarditis; myxoviruses, for example, Influenza A₂ (Jap/305); arboviruses, for example, Semliki Forest; herpesvirus group, for example, herpes simplex; and poxviruses, for example, Vaccinia IHD. When administered prior to infection, that is, prophylactically, it is preferred that the administration be within 0 to 96 hours prior to infection of the animal with pathogenic virus. When administered thereapeutically to inhibit an infection, it is preferred that the administration be within about a day or two after infection with pathogenic virus.

The dosage administered will be dependent upon the virus for which treatment or prophylaxis is desired, the type of animal involved, its age, health, weight, extent of infection kind of concurrent treatment, if any, frequency of treatment, and the nature of the effect desired. Illustratively, dosage levels of the administered active ingredients can be: intravenously, 0.1 to about 10 mg/kg; intraperitoneal, 0.1 to about 50 mg/kg; subcutaneous, 0.1 to about 250 mg/kg; orally, 0.1 to about 500 mg/kg and preferably about 1 to 250 mg/kg; intranasal instillation, 0.1 to about 10 mg/kg; and aerosol, 0.1 to about 10 mg/kg of animal body weight.

The compounds may be administered, dissolved or suspended, in any conventional non-toxic pharmaceutical carrier of the type that may be taken orally, applied topically, buccally or parenterally.

The compounds of the present invention may be prepared by various methods such as, for example, according to the methods described below in the several reaction schemes illustrated by the equations and in the specific examples.

Reaction Scheme 1

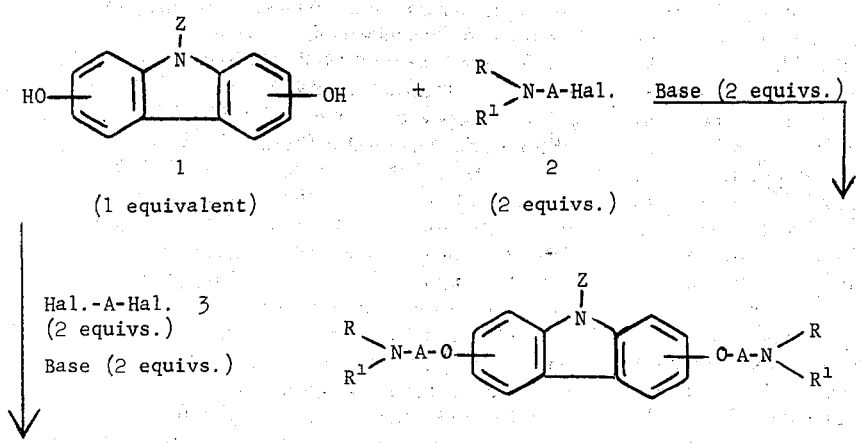

Formula II

Reaction Scheme 2

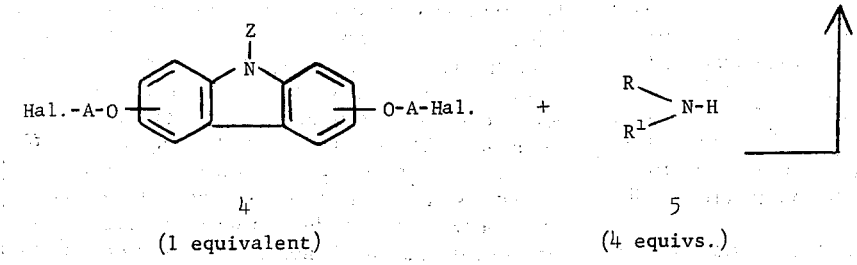

Reaction Scheme 3

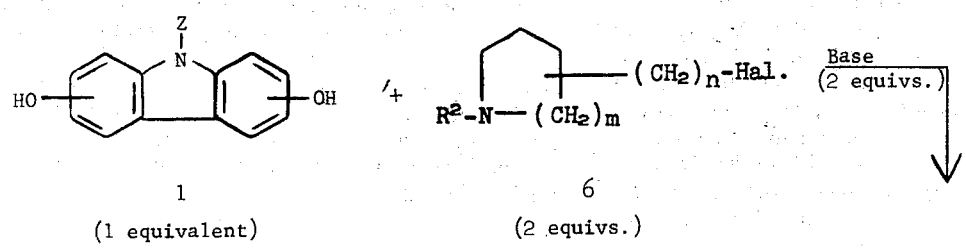

Formula III

Formula III

In the above reaction schemes Z, R, R¹, A, R², m, and n have the same meanings specified hereinbefore, and each Hal. is chlorine, bromine or iodine.

Typical haloalkylamines, 2, useful in Reaction Scheme 1 are for example, N,N-diethyl-2-chloroethylamine, N-(2-chloroethyl)piperidine and the like. Typical dihaloalkanes, 3, useful in Scheme 2 are for example, 1-bromo-2-chloroethane, 1,6-dibromohexane and the like. Amines, 5, useful in Reaction Scheme 2 are primary amines such as, for example, ethylamine, or secondary amines, such as, for example, dimethylamine, or tertiary amines, such as, for example, hexamethylenetetramine and the like. Typical of the halogen substituted heterocyclic nitrogen compounds, 6, useful in Reaction Schemes 3 are for example, 3-chloromethyl-1-methylpiperidine and the like.

In the above reaction the base used may be for example, sodium methoxide, sodium hydride, sodium amide, sodium hydroxide, potassium hydroxide and the like. Solvents used as the reaction medium may vary over a wide range of solvent types and include aromatic hydrocarbons such as benzene, toluene, xylene and the like; halogenated aromatics, such as chloro-benzene and the like; aprotic solvents such as N,N-dimethylformamide, N,N-dimethylacetamide, dimethyl sulfoxide and the like; alcohols such as ethanol, isopropanol and the like; ketones such as acetone, butanone and the like; ethers such as tetrahydrofuran, dioxane and the like; water; or mixtures of these solvents.

In the method of synthesis where either sodium methoxide, sodium amide or sodium hydride, for example, is used as the base, the reaction is carried out in an anhydrous medium, such as anhydrous toluene, chlorobenzene and the like. About 2.5 equivalents of the base is added to a suspension of, for example, 1 equivalent of a carbazolediol, compound 1, in the anhydrous solvent, and the mixture heated to form the diphenoxide. In the case where sodium methoxide is used, the methanol formed may be removed advantageously by azeotropic distillation. About 2.5 equivalents of the halide, 2, 3 or 6, is then added and the mixture heated to reflux for a period which may vary from about 4 to 24 hours. The products, that is, compounds of Formula II and III and compound 4 are then isolated by customary procedures. Compounds of Formula II and III are usually isolated as bis-acid addition salts.

In the method where an alkali hydroxide, such as potassium hydroxide, for example, is used as the base, two different procedures may be used. In the one procedure a 25 to 50 per cent aqueous solution of the alkali hydroxide (about 2.5 equivalents) is added to a suspension of, for example, 1 equivalent of compound 1 in a suitable aromatic solvent, such as, for example, xylene. This mixture is then heated to boiling, with stirring and the water removed by azeotropic distillation, a convenient method being to collect the water in a device such as the Dean-Stark distilling receiver. The reaction mixture, now being essentially anhydrous, is treated with about 2.5 equivalents of the halide, compound 2, 3 or 6, as described above. In the other procedure the reaction is carried out in a heterogeneous medium of water and an aromatic hydrocarbon, such as, for example, toluene, xylene and the like. For example, 1 equivalent of compound 1 is suspended in the aromatic hydrocarbon. Then in Reaction Schemes 1 and 3, a solution of about 2.5 equivalents of a hydrohalide salt of the haloalkylamine, that is, a hydrohalide salt of compound 2 or 6, in the minimum volume of water is added and with efficient stirring, a 25 to 50 per cent solution of the alkali hydroxide (about 5 equivalents) is added. The mixture is heated to reflux for a period of about 6 to 24 hours, and the product isolated from the hydrocarbon layer. In Reaction Scheme 2, with the aqueous/aromatic hydrocarbon medium is used to prepare compounds of type 4, which contain no amine functions, the amount of alkali hydroxide used is only in slight excess of 2.0 equivalents per 1 equivalent of diphenol that is, compound 1.

In Reaction Scheme 2, the reaction between the bis($\omega$-haloalkyl)-ether, 4, and the amine, 5, may be carried out under a variety of conditions. For example, the compound 4 may be heated together with a large excess of the amine, 5, the excess amine serving as both the reaction medium and the hydrohalide acceptor. This method is particularly suitable for readily available amines, the excess of which can be easily removed from the reaction mixture by, for example, distillation at reduced pressure or by steam distillation. Or, 1 equivalent of the bis($\omega$-haloalkyl)ether, 4, and 4 equivalents of the amine, 5 may be heated together in one of a number of different types of solvents, for example, in aromatic solvents, such as, benzene, toluene, xylene, chlorobenzene and the like; or lower molecular weight alcohols, such as, methanol, ethanol, isopropyl alcohol and the like; or lower molecular weight ketones, such as, acetone, methyl ethyl ketone and the like. The reaction between the halo compound and the amine is usually promoted by the addition of either sodium or potassium iodide, the iodide being used in either catalytic or stoichiometric amounts. In some cases, it may be advantageous to use only two equivalents of the amine, 5, for each equivalent of the bis($\omega$-haloalkyl)ether, an excess of either powdered sodium or potassium carbonate being used as the acceptor for the hydrohalide generated. In the case of volatile amines, this reaction may be best carried out under pressure in a suitable bomb or autoclave.

Reaction Scheme 4

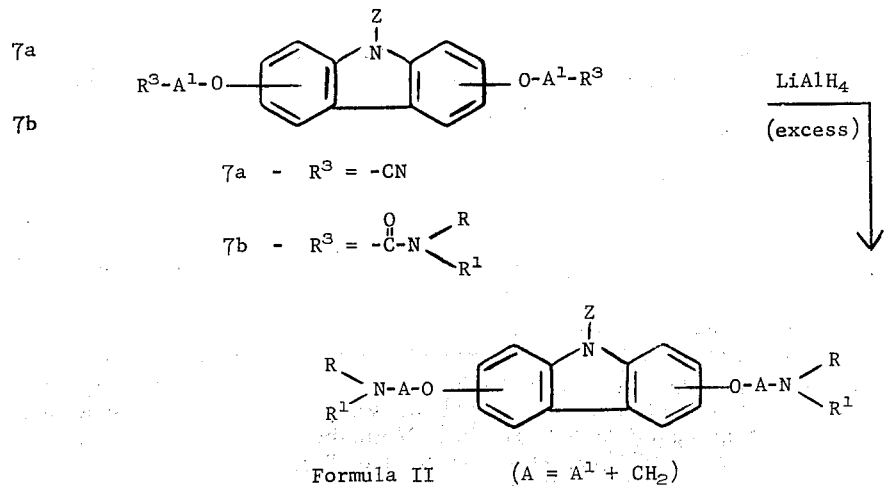

7a   -   $R^3$ = -CN

7b   -   $R^3$ = -C(=O)-N(R)(R^1)

Formula II   (A = $A^1$ + $CH_2$)

In this scheme of synthesis, R, R¹, A, and Z have the same meanings specified hereinbefore, and A¹ is an alkylene chain having one less methylene, —CH₂—, group in a straight chain than does A, that is, A = A¹ + CH₂.

The intermediate nitriles, 7a, and amides, 7b, may be prepared by the method illustrated, for example, in Reaction Scheme 1 above, in which the appropriate ω-haloalkyl nitriles and amides are substituted for the haloalkylamines, 2.

According to the method of preparation illustrated in Reaction Scheme 4, compounds of Formula II, in which both R and R¹ are hydrogen, may be prepared from either the nitriles, 7a, or the unsubstituted amides, 7b, wherein R = R¹ = H. Secondary amines, that is, compounds of Formula II wherein R is H and R¹ is not H, can also often be prepared by this method from the corresponding secondary amides, 7b, wherein R is H and R¹ is not H.

appropriate acyl halides or anhydrides, followed by reduction of the N-acyl amines with lithium aluminum hydride.

Reductive alkylation of the primary amines with an excess of the appropriate aldehydes or ketones in the presence of molecular hydrogen and a catalyst, such as platinum or Raney nickel, for example, will yield the symmetrically substituted tertiary amines, that is, compounds of Formula II wherein R = R¹ but neither is H. Alkylation of the primary amines with formaldehyde and formic acid by the Eschweiler-Clarke procedure yields the tertiary amines of Formula II in which R = R¹ = CH₃.

Alkylation of the primary amines with a large excess of the appropriate halides yields the symmetrically substituted tertiary amines, that is, compounds of Formula II wherein R = R¹ but neither is H.

Alkylation of the secondary amines, that is, compounds of Formula II wherein R is H and R¹ is not H by Reaction Scheme 5

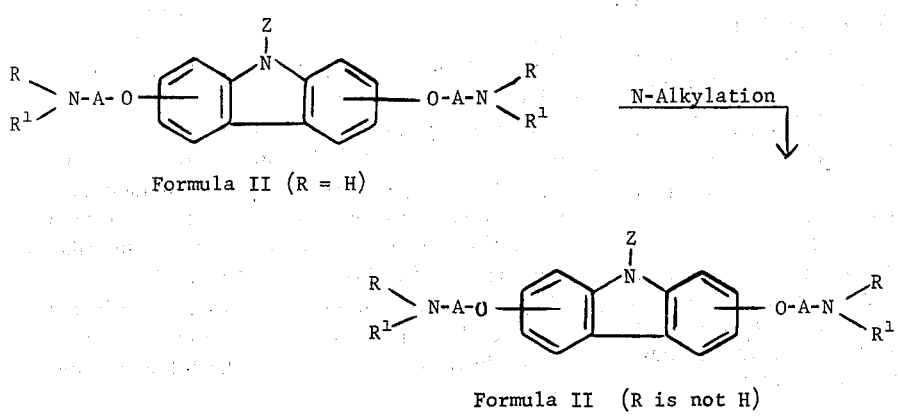

Formula II (R = H)

Formula II (R is not H)

In this reaction scheme R¹, A, and Z have the same meanings specified hereinbefore, and with the exceptions noted in the two formulas above, R has the same meaning specified hereinbefore.

Alkylation of the primary amines, that is, compounds of Formula II wherein each R and R¹ is H, by the method illustrated in Reaction Scheme 5 may be used to prepare either the secondary amines, that is, compounds of Formula II wherein R is H and R¹ is not H, or the symmetrically substituted tertiary amines, that is, compounds of Formula II wherein R = R¹ but neither is H.

One method for preparing the secondary amines, that is, compounds of Formula II wherein R is H and R¹ is not H, is the reaction of the primary amines, that is, compounds of Formula II wherein each R and R¹ is H with the stoichiometric quantities of the appropriate aldehydes or ketones to yield the corresponding Schiff's bases, which may then be reduced with either a borohydride or molecular hydrogen in the presence of a catalyst, such as platinum or Raney nickel, for example. Another method for preparing the secondary amines is acylation of the primary amines with the the method illustrated in Reaction Scheme 5 may be used to prepare either the symmetrically substituted tertiary amines, that is, compounds of Formula II wherein R = R¹ but neither is H or the unsymmetrically substituted tertiary amines, that is, compounds of Formula II wherein R and R¹ are different and neither is H.

Reaction of the secondary amines with the appropriate halides is one method for effecting N-alkylation. Another useful method is the reductive alkylation of the secondary amines with the appropriate aldehydes or ketones in the presence of molecular hydrogen and a catalyst, such as platinum or Raney nickel, for example. Another useful alkylation method is the two-step whereby the secondary amines are acylated with the appropriate acyl halides or anhydrides and the resulting N-acyl amines are reduced with lithium aluminum hydride to the corresponding tertiary amines. Alkylation of the secondary amines with formaldehyde and formic acid by the Eschweiler-Clarke procedure is a method for preparing the tertiary amines of Formula II in which R = CH₃.

Another useful method for preparing the bis-basic ethers represented by Formulas II and III is illustrated in Reaction Scheme 6.

Reaction Scheme 6

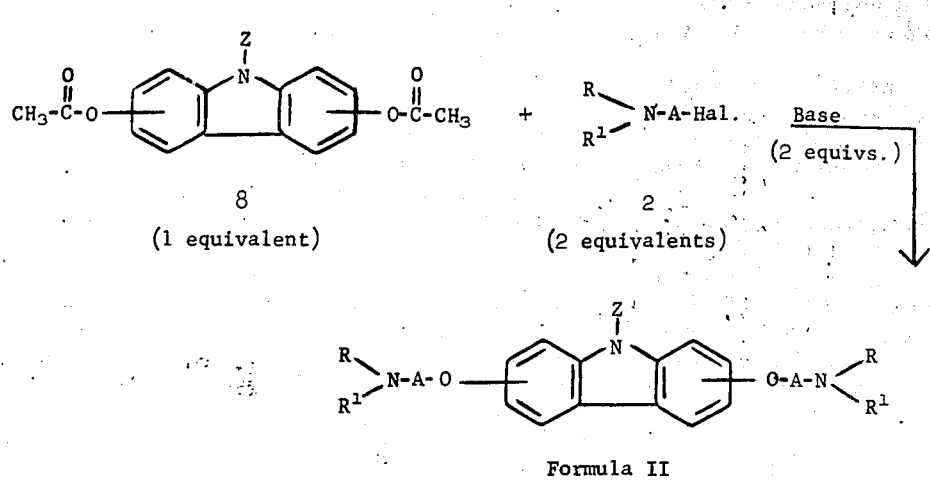

Formula II

This method is equally applicable to the preparation of bis-basic ethers represented by Formula III, in which case haloalkylamines of type 6 are substituted for the type 2 haloalkylamines shown in the above illustration.

By the method of Reaction Scheme 6, the bis-basic ethers can be prepared directly from the diacetates of carbazole-diols, that is, compound 8, which in many cases are more conveniently isolated than are the diols particularly, since the latter are somewhat susceptible to air oxidation and difficult to purify.

In this procedure, it is often advantageous to use the hydrochloride salt of the haloalkylamine, 2 or 6, in place of the base form, in which case, the amount of base is doubled. Conveniently, the base used can be an alkali alkoxide, such as sodium methoxide, sodium ethoxide and the like. Solvents used in this procedure include aromatic hydrocarbons, such as benzene and toluene, and halogenated aromatics, such as chlorobenzene and the like. Reaction conditions can vary over a wide range with respect to the reaction period and temperature; however, the reaction is generally effected at the reflux temperature of the solvent for a period of 6 to 72 hours. The preferred method is to heat a mixture of compound 8, the hydrochloride salt of compound 2 or 6, and four equivalents of sodium methoxide in refluxing chlorobenzene for 24 hours.

As compounds of this invention are prepared by reaction schemes 1, 3 or 6, or the intermediates for reaction schemes 2 or 4, in which Z is hydrogen, certain precautions should be taken to avoid N-alkylation of the carbazole ring. In general O-alkylation proceeds under much milder reaction conditions and preferentially to N-alkylation. Conditions suitable for the preparation of the desired compounds are those in which only the minimal necessary amounts of alkylating agent and/or base are used to obtain O-alkylation to the exclusion of N-alkylation. Lower temperatures are generally effective for O-alkylation in contrast to the need for higher temperatures and strictly anhydrous conditions for N-alkylation.

Starting materials which find use in preparing the compounds illustrated in the above reaction schemes and in the specific examples given below are the following carbazole-diols, that is, compound 1: 1,7-dihydroxycarbazole [I. G. Farbenind. A-G., U.S. Pat. No. 1,981,301, Nov. 20, 1934; CA 28:1050]; 1,8-dihydroxycarbazole [I. G. Farbenind. A-G., British Pat. No. 341,905, Jan. 14, 1931; CA 23:3715]. The 3,6-dihydroxycarbazole can be prepared by hydrolysis of 3,6-carbazolediol diacetate.

The diacetates, 8, can be obtained by acetylation of the above described diols, and the diacetate of 3,6-dihydroxy-N-alkylcarbazole can be obtained directly by the Baeyer-Villiger oxidation of 3,6-diacetyl-N-alkyl-carbazole by the general procedures described in C. Hassal, *Organic Reactions* 9, 73 (1957).

Representative compounds of the present invention and several of the methods for preparing them, mentioned above, are illustrated in the following specific examples.

EXAMPLE 1

N-ETHYL-3,6-CARBAZOLEDIOL

To 700 ml of water containing 80 g (2.0 mole) of sodium hydroxide was added 85 g (0.27 mole) of N-ethyl-3,6-carbazolediol diacetate. The reaction mixture was heated for one hour then acidified with 3N hydrochloric acid to give the product which was recrystallized from ethanolwater. M.P. 190°–200°C (dec.).

EXAMPLE 2

3,6-BIS(2-DIETHYLAMINOETHOXY)-N-ETHYL-CARBAZOLE BIS-DIHYDROGEN CITRATE HEMIHYDRATE

To 350 ml of water containing 25 g (0.62 mole) of sodium hydroxide was added 22.7 g (0.1 mole) of N-ethyl-3,6-carbazolediol, 68.7 g (0.4 mole) of 2-diethylaminoethylchloride hydrochloride and 700 ml of toluene. The heterogeneous reaction mixture was refluxed with stirring for 24 hours, after which the toluene layer was separated, washed with several portions of water, dried and evaporated in vacuo. The resulting oily residue was purified by column chromatography on alumina using ether as the eluant. The product was converted to the bis-dihydrogen citrate salt and recrystallized from methanol-butanone. M.P. 100–105°C, $\lambda_{max}^{EtOH}$ 233, $E_{1cm}^{1\%}$ 516.

EXAMPLE 3

3,6-BIS(2-DIETHYLAMINOETHOXY)-N-ETHYL-CARBAZOLE DIHYDROCHLORIDE

A mixture of 15.5 g (0.05 mole) of N-ethyl-3,6-carbazolediol diacetate, 17.2 g (0.1 mole) of 2-diethylaminoethylchloride hydrochloride, 10.8 g (0.2 mole) of sodium methoxide and 400 ml. of chlorobenzene was refluxed for 24 hours. Upon cooling, the reaction mixture was filtered, and the filtrate was washed with several portions of water, dried over anhydrous magnesium sulfate, diluted with ether and acidified with ethereal HCl. The resulting precipitate was separated and recrystallized from methanol-ethyl acetate to give the desired product. M.P. 208°–210°C, $\lambda_{max}^{EtOH}$ 232, $E_{1cm}^{1\%}$ 853.

EXAMPLE 4

3,6-BIS(3-DIMETHYLAMINOPROPOXY)-N-ETHYLCARBAZOLE DIHYDROCHLORIDE

Following the procedure of Example 3, only substituting for 2-diethylaminoethylchloride hydrochloride, 15.8 g (0.1 mole) of 3-dimethyl-aminopropylchloride hydrochloride, the desired product was obtained. M.P. 239°–240°C, $\lambda_{max}^{EtOH}$ 231, $E_{1cm}^{1\%}$ 883.

EXAMPLE 5

N-ETHYL-3,6-BIS(2-PIPERIDINOETHOXY)CARBAZOLE DIHYDROCHLORIDE

Following the procedure of Example 3 only substituting for 2-diethylaminoethylchloride hydrochloride, 18.4 g (0.1 mole) of 2-piperidino-ethylchloride hydrochloride, the desired product was obtained. M.P. 248°–250°C, $\lambda_{max}^{EtOH}$ 232, $E_{1cm}^{1\%}$ 830.

EXAMPLE 6

1,8-BIS(2-DIETHYLAMINOETHOXY)CARBAZOLE BIS-DIHYDROGEN CITRATE

Following the procedure of Example 2, only substituting for N-ethyl-3,6-carbazolediol, 19.9 g (0.1 mole) of 1,8-carbazolediol and using 37.8 g (0.22 mole) of 2-diethylaminoethyl chloride hydrochloride, the desired product is obtained

EXAMPLE 7

3,6-BIS(2-DIETHYLAMINOETHOXY)-N-METHYLCARBAZOLE BIS-DIHYDROGEN CITRATE

Following the procedure of Example 2, only substituting for N-ethyl-3,6-carbazolediol, 21.3 g (0.1 mole) of N-methyl-3,6-carbazolediol, the desired product is obtained.

EXAMPLE 8

3,6-BIS(2-DIHEXYLAMINOETHOXY)-N-ETHYL-CARBAZOLE DIHYDROCHLORIDE

Following the procedure of Example 3, only substituting for 2-diethylaminoethylchloride hydrochloride, 28.4 g (0.1 mole) of 2-dihexyl-aminoethylchloride hydrochloride, the desired product is obtained.

EXAMPLE 9

3,6-BIS(2-ETHYLAMINOETHOXY)-N-ETHYL-CARBAZOLE DIHYDROCHLORIDE

A. To a stirred mixture of 31.1g (0.1 mole) of N-ethyl-3,6-carbazolediol diacetate and 39.4 g (0.3 mole) of 1-bromo-2-chloroethane in 400 ml of chlorobenzene is added 0.2 mole of sodium methoxide. Upon complete addition of the alkali, the mixture is refluxed with stirring for 18 hours, then cooled. The supernatant water layer is decanted and the residue is taken up in ethanol. The solid which separates is filtered and recrystallized from ethanol-chloroform to give 3,6-bis(2-chloroethoxy)-N-ethylcarbazole.

B. A mixture of 35.2 g (0.1 mole) of 3,6-bis(2-chloroethoxy)-N-ethylcarbazole, 4.5 g (0.1 mole) of ethylamine, 2.0 g of potassium iodide and 100 ml of tetrahydrofuran is heated with stirring at 110°C for 24 hours in a Paar pressure reactor. The solvent is removed in vacuo, and the remaining residue is treated with dilute sodium hydroxide and ether. The ether layer is washed twice with water, dried over magnesium sulfate and acidified with ethereal HCl to give the desired product which is recrystallized from methanol-ethyl acetate.

EXAMPLE 10

3,6-BIS(2-AMINOETHOXY)-N-ETHYLCARBAZOLE DIHYDROCHLORIDE

Following the procedure of Example 9B, only substituting for ethylamine, the appropriate molar equivalent amount of hexamine, and subsequently decomposing the intermediate quaternary ammonium complex with dilute acid, the desired product is obtained.

EXAMPLE 11

3,6-BIS(6-DIMETHYLAMINOHEXYLOXY)-N-ETHYLCARBAZOLE DIHYDROCHLORIDE

Following the procedure of Example 9A, only substituting for 1-bromo-2-chloroethane, 59.8 g (0.3 mole) of 6-bromo-1-chlorohexane, the intermediate 3,6-bis(6-chlorohexyloxy)-N-ethylcarbazole is obtained.

Following the procedure of Example 10B, only substituting respectively for 3,6-bis(2-chloroethoxy)-N-ethylcarbazole and ethylamine, the appropriate molar equivalent amount of 3,6-bis(6-chlorohexyloxy)-N-ethylcarbazole and an excess of diethylamine, the desired product is obtained.

EXAMPLE 12

1,7-BIS(2-DIETHYLAMINOETHOXY)CARBAZOLE BIS-DIHYDROGEN CITRATE

Following the procedure of Example 2, only substituting for N-ethyl-3,6-carbazolediol, 19.9 g (0.1 mole) of 1,7-carbazolediol, and using 37.8 g (0.22 mole) of 2-diethylaminoethyl chloride hydrochloride, the desired product is obtained.

EXAMPLE 13

3,6-BIS[2-(DIMETHYLAMINO)-1-METHYLETHOXY]-N-ETHYLCARBAZOLE DIHYDROCHLORIDE

Following the procedure of Example 3, only substituting for 2-diethylaminochloride hydrochloride, 15.8 g (0.1 mole) of 2-(dimethyl-amino)-1-methylethylchloride hydrochloride, the desired product is obtained.

EXAMPLE 14

N-ETHYL-3,6-BIS[(1-METHYL-3-PIPERIDYL)METHOXY]CARBAZOLE DIHYDROCHLORIDE

Following the procedure of Example 3 only substituting for 2-diethylaminoethylchloride hydrochloride, the appropriate molar equivalent amount of 3-chloromethyl-1-methylpiperidine, the desired product is obtained.

EXAMPLE 15

N-ETHYL-3,6-CARBAZOLEDIOL DIACETATE

To a solution of 104 g (0.37 mole) of 3,6-diacetyl-N-ethylcarbazole in 1700 ml of chloroform (hydrocarbon stabilized) previously cooled to 15°C was added 138 g (0.8 mole) of m-chloroperbenzoic acid. The reaction was stirred at room temperature for 4 days, then filtered. The filtrate was washed with saturated sodium bicarbonate solution and with water, then dried over anhydrous magnesium sulfate and evaporated to dryness in vacuo leaving a solid which was recrystallized from acetone-water and then from acetone methanol to give the desired product. M.P. 138°–139°C, $\lambda_{max}^{EtOH}$ 237, $E_{1cm}^{1\%}$ 1330.

What is claimed is:

1. A compound selected from a base of the formula

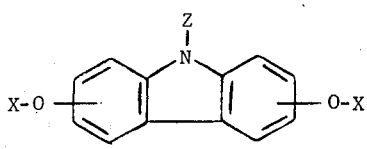

wherein Z is selected from the group consisting of hydrogen or lower alkyl; and each X is a member selected from the group consisting of A. the group

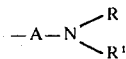

wherein each A is a straight or branched alkylene chain having from 2 to 6 carbon atoms; R and $R^1$ are individually selected from the group consisting of hydrogen or lower alkyl having from 1 to 6 carbon atoms; or each set of R and $R^1$ taken together with the nitrogen atom to which they are attached is a saturated monocyclic heterocyclic group selected from pyrrolidino or piperidino; or B. the group

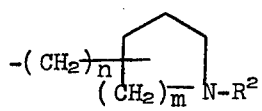

wherein $n$ is a whole integer from 0 to 2, $m$ is 1 or 2, and $R^2$ is a member selected from the group consisting of hydrogen or lower alkyl having from 1 to 4 carbon atoms; or a pharmaceutically acceptable acid addition salt of said base.

2. A compound of claim 1 wherein each X is the group

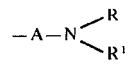

wherein each R and $R^1$ is selected from the group consisting of hydrogen or lower alkyl having from 1 to 6 carbon atoms, or each set of R and $R^1$ taken together with the nitrogen atom to which they are attached is a saturated monocyclic heterocyclic group selected from pyrrolidino or piperidino; and wherein one of the

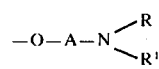

groups is in the 3-position of the carbazole ring system, and the other such group is in the 6-position of the carbazole ring system.

3. A compound of claim 2 wherein each A is a lower alkylene chain having from 2 to 4 carbon atoms and wherein each R and $R^1$ is lower alkyl having from 1 to 4 carbon atoms.

4. A compound of claim 2 which is 3,6-bis[2-(diethylamino)-ethoxy]-N-ethylcarbazole bis-dihydrogen citrate.

5. A compound of claim 2 which is 3,6-bis[3-(dimethylamino)-propoxy]-N-ethylcarbazole or a pharmaceutically acceptable acid addition salt thereof.

6. A compound of claim 2 which is N-ethyl-3,6-bis(2-piperidino-ethoxy)carbazole or a pharmaceutically acceptable acid addition salt thereof.

7. A compound of claim 1 wherein each X is the group

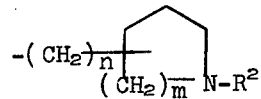

and one of said —O—X groups is in the 3-position of the carbazole ring system and the remaining —O—X group is in the 6-position of the carbazole ring system.

* * * * *

UNITED STATES PATENT OFFICE
CERTIFICATE OF CORRECTION

PATENT NO. : 3,932,424
DATED : January 13, 1976
INVENTOR(S) : Wm. L. Albrecht and Robert W. Fleming It is certified that error appears in the above-identified patent and that said Letters Patent are hereby corrected as shown below:

Column 2 of the Abstract, after the first formula, patent should read "wherein Z is hydrogen or lower alkyl having from 1 to 4 carbon atoms; and each X is A. the group $-A-N\begin{smallmatrix}R\\R^1\end{smallmatrix}$ wherein each A is a straight or branched alkeylene".

Column 8, line 13, "with the aqueous" should read "when the aqueous". Column 14, line 38, "3,6-Bis(6-Dimethylamino...." should read "3,6-Bis(6-Diethylamino......".

Signed and Sealed this twenty-second Day of June 1976

[SEAL]

Attest:

RUTH C. MASON
Attesting Officer

C. MARSHALL DANN
Commissioner of Patents and Trademarks